(12) United States Patent
Shin et al.

(10) Patent No.: US 8,043,355 B2
(45) Date of Patent: Oct. 25, 2011

(54) DOUBLE-TUBE TYPE STENT

(75) Inventors: Kyong-Min Shin, Seoul (KR);
Jeung-Hee Nam, Kimpo-si (KR)

(73) Assignees: Taewoong Medical Co., Ltd.,
Kyunggi-do (KR); Kyong-Min Shin,
Seoul (KR)

( * ) Notice: Subject to any disclaimer, the term of this patent is extended or adjusted under 35 U.S.C. 154(b) by 0 days.

(21) Appl. No.: 12/344,609

(22) Filed: Dec. 29, 2008

(65) Prior Publication Data

US 2009/0192627 A1 Jul. 30, 2009

(30) Foreign Application Priority Data

Jan. 29, 2008 (KR) .................. 10-2008-0009089

(51) Int. Cl.
*A61F 2/06* (2006.01)
(52) U.S. Cl. .................. 623/1.13; 623/1.44; 623/1.46
(58) Field of Classification Search .................. 623/1.1, 623/1.18–1.19, 1.51, 23.7, 1.13, 1.44, 1.46, 623/1.52–1.53, 23.64, 1.47
See application file for complete search history.

(56) References Cited

U.S. PATENT DOCUMENTS

| | | | | |
|---|---|---|---|---|
| 5,061,276 A | * | 10/1991 | Tu et al. ................ | 623/1.33 |
| 5,827,321 A | * | 10/1998 | Roubin et al. ............ | 623/1.16 |
| 6,096,070 A | * | 8/2000 | Ragheb et al. ............ | 623/1.39 |
| 6,156,064 A | * | 12/2000 | Chouinard ................ | 623/1.44 |
| 6,197,014 B1 | * | 3/2001 | Samson et al. ............ | 604/524 |
| 6,537,310 B1 | * | 3/2003 | Palmaz et al. ............ | 623/1.13 |
| 6,626,939 B1 | * | 9/2003 | Burnside et al. .......... | 623/1.38 |
| 6,733,524 B2 | * | 5/2004 | Tseng et al. ............. | 623/1.46 |
| 6,939,372 B2 | * | 9/2005 | Dong .................... | 623/1.13 |
| 7,462,192 B2 | * | 12/2008 | Norton et al. ............ | 623/1.53 |
| 7,722,664 B2 | * | 5/2010 | Zarbatany et al. ......... | 623/1.35 |
| 7,744,645 B2 | * | 6/2010 | Thornton et al. ......... | 623/1.46 |
| 2002/0107565 A1 | * | 8/2002 | Greenhalgh .............. | 623/1.24 |
| 2004/0148007 A1 | * | 7/2004 | Jackson et al. ........... | 623/1.12 |
| 2004/0148010 A1 | * | 7/2004 | Rush .................... | 623/1.13 |
| 2004/0167606 A1 | * | 8/2004 | Chouinard ................ | 623/1.13 |
| 2006/0155369 A1 | * | 7/2006 | Edwin et al. ............. | 623/1.42 |
| 2007/0207186 A1 | * | 9/2007 | Scanlon et al. ........... | 424/424 |
| 2008/0009934 A1 | * | 1/2008 | Schneider et al. ......... | 623/1.11 |
| 2008/0183272 A1 | * | 7/2008 | Wood et al. ............. | 623/1.11 |
| 2009/0082840 A1 | * | 3/2009 | Rusk et al. .............. | 623/1.11 |

* cited by examiner

*Primary Examiner* — Paul Prebilic
(74) *Attorney, Agent, or Firm* — IP & T Group LLP

(57) ABSTRACT

A double-tube type stent is inserted into a hollow tubular organ such as a bile duct so as to relieve narrowing of the bile duct on, for instance, an anastomotic area of the intrahepatic bile duct of a liver transplant patient. A hollow cylindrical body has a plurality of rhombic spaces formed by weaving a superelastic shape-memory-alloy wire so as to be crossed. A silicon coating layer is coated on an outer surface of the cylindrical body using a silicon solution. A polytetrafluoroethylene (PTFE) tube is fixedly fitted around the cylindrical body having the silicon coating layer leaving a gap therebetween.

3 Claims, 3 Drawing Sheets

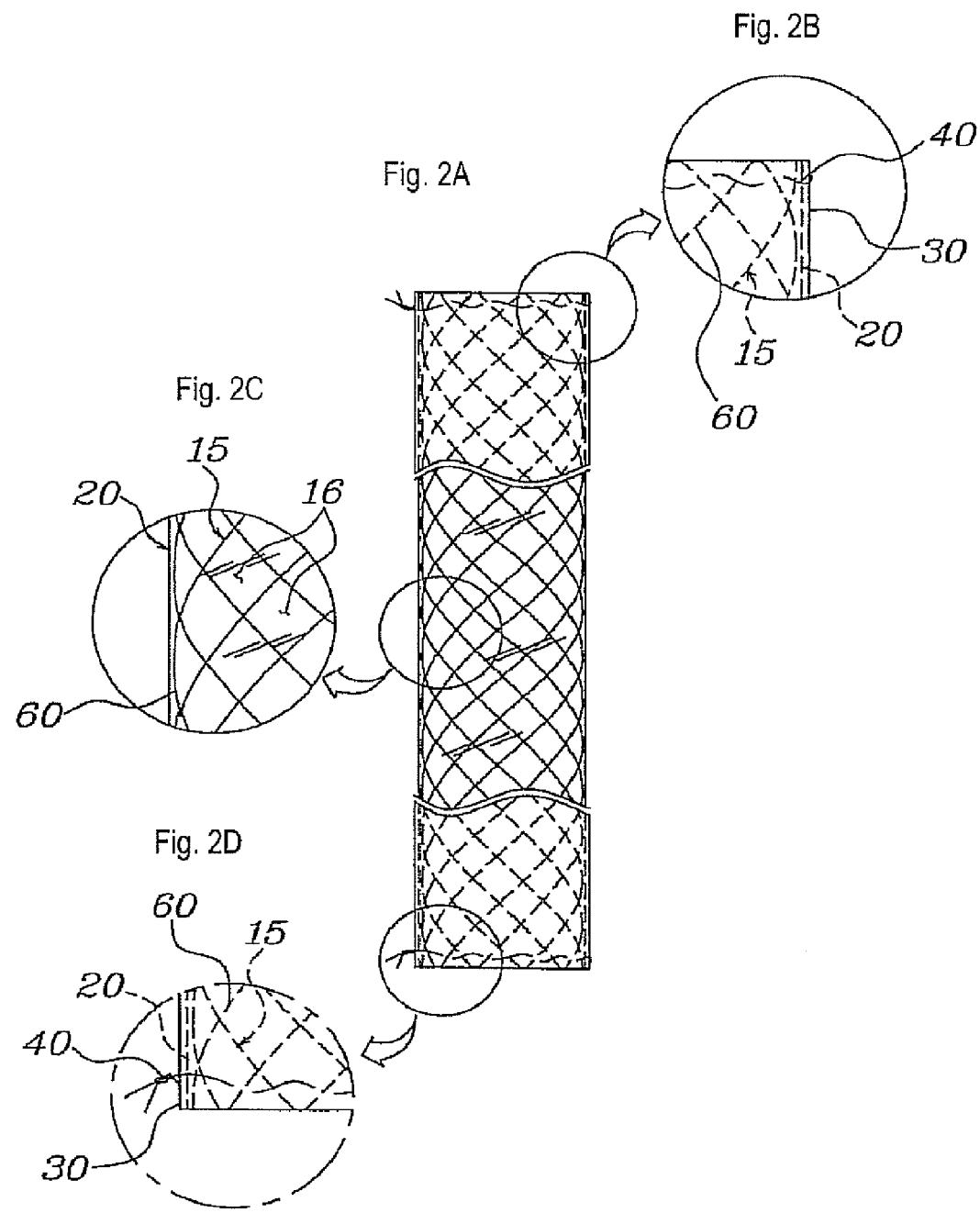

DOUBLE-TUBE TYPE STENT

BACKGROUND OF THE INVENTION

1. Field of the Invention

The present invention relates, in general, to a stent that is inserted into a hollow tubular organ such as a bile duct to relieve narrowing of the hollow tubular organ, for instance, on an anastomotic area of the intrahepatic bile duct of a liver transplant patient and, more particularly, to a double-tube type stent having a dual protection structure in which a silicon coating layer is formed on the outer surface of a hollow cylindrical body woven with a superelastic shape-memory-alloy wire using a silicon solution, in which a polytetrafluoroethylene (PTFE) tube is fitted around the cylindrical body having the silicon coating layer leaving a gap therebetween, thereby providing maximum durability, long-term usability and safe removal with respect to the hollow tubular organ.

2. Description of the Related Art

Generally, when a hollow tubular organ, for instance a bile duct, on an anastomotic area of the intrahepatic bile duct of a liver transplant patient, is narrowed, causing a chance of blocking a flow of bile, a request is made to improve the flow of bile.

This improvement of the flow of bile has been mainly accomplished by relieving the narrowing of the bile duct using a stent.

In detail, as illustrated in FIG. 1, the stent 1 which is used is made by weaving a superelastic shape-memory-alloy wire so as to be crossed and thereby form a hollow cylindrical body 3 having a plurality of rhombic spaces 2.

At this time, the stent 1 is used to smoothly guide the flow of bile after a silicon coating layer is formed or after it is covered with a polytetrafluoroethylene (PTFE) tube.

When the silicon coating layer is formed on the stent 1, the silicon coating layer has a lubricating characteristic, and thus smoothly guides the bile in the bile duct. However, the silicon coating layer reduces flexibility, and thus makes it difficult to maintain the stent in the bile duct for a long time.

Further, due to the strongly acidic environment inside the bile duct, the silicon coating layer is dissolved, reducing durability. For this reason, in the case of the stent having such a silicon coating layer, the stent must be typically changed out approximately every three months.

In the case in which the stent is covered with the PTFE tube, the stent is maintainable in the bile duct for a long time due to flexibility of the PTFE tube. Nevertheless, the PTFE tube does not come into contact with the stent, and fails to be firmly fixed to the stent. Accordingly, the PTFE tube brings about inconvenient use, and fails to effectively guide the bile.

More specifically, the PTFE tube is fixed to the stent in such manner that upper and lower ends thereof are tied with a thread. However, since the thread is directly tied to the stent, it does not maintain a firmly tied state due to sliding, or the like.

Moreover, in the case in which only the silicon coating layer is formed on the stent 1, or in which only the PTFE tube is covered on the stent 1, a lesion area of the bile duct cannot be prevented from protruding through the rhombic spaces 2 formed on the outer surface of the stent 1.

In other words, since only one of the silicon coating layer and the PTFE tube has low resistance, it cannot prevent the lesion area of the bile duct from protruding, particularly, from protruding through the rhombic spaces 2 formed on the outer surface of the stent 1. Thus, bleeding occurs through the protruding lesion area of the bile duct. When the stent is to be removed, it is impossible to do so without cutting off the protruding lesion area of the bile duct.

SUMMARY OF THE INVENTION

Accordingly, the present invention has been made keeping in mind the above problems occurring in the related art, and embodiments of the present invention provide a double-tube type stent having a dual protection structure in which a silicon coating layer is formed on the outer surface of a hollow cylindrical body woven with a superelastic shape-memory-alloy wire using a silicon solution and in which a polytetrafluoroethylene (PTFE) tube is fitted around the cylindrical body having the silicon coating layer with a gap remaining in between them, thereby providing maximum durability and long-term usability in the bile duct, and blocking the protrusion of a lesion area of the bile duct to prevent bleeding, and maximizing reliability owing to safe removal from the bile duct.

According to one aspect of the present invention, there is provided a double-tube type stent, which includes a hollow cylindrical body having a plurality of rhombic spaces by weaving a superelastic shape-memory-alloy wire so as to be crossed, a silicon coating layer coated on an outer surface of the cylindrical body using a silicon solution, and a polytetrafluoroethylene tube fixedly fitted around the cylindrical body having the silicon coating layer leaving a gap therebetween.

In an embodiment of the present invention, the polytetrafluoroethylene tube may be tied to upper and lower ends of the cylindrical body having the silicon layer with a thread so as to be fixed to the cylindrical body.

According to embodiments of the present invention, the double-tube type stent has a dual protection structure in which a silicon coating layer is formed on the outer surface of a hollow cylindrical body woven with a superelastic memory alloy wire using a silicon solution, and in which a polytetrafluoroethylene (PTFE) tube is fitted around the cylindrical body having the silicon coating layer leaving a gap therebetween, so that the silicon coating layer is protected from the strongly acidic bile inside the bile duct, thereby providing maximum durability and long-term usability in the bile duct.

Further, a lesion area of the bile duct is blocked to prevent bleeding thanks to the dual protection structure of the PFTE tube and the silicon coating layer, particularly due to a buffer function of the gap between the PFTE tube and the silicon coating layer. In addition, the double-tube type stent is safely removable from the bile duct without separately cutting off the protrusion of the lesion area, thereby maximizing reliability of use.

BRIEF DESCRIPTION OF THE DRAWINGS

The above and other objects, features and advantages of the present invention will be more clearly understood from the following detailed description when taken in conjunction with the accompanying drawings, in which:

FIGS. 1A and 2B are views illustrating a conventional biliary stent;

FIGS. 2A, 2B, 2C, and 2D are views illustrating a double-tube type stent according to an exemplary embodiment of the present invention;

DETAILED DESCRIPTION OF THE INVENTION

Figure 1A:
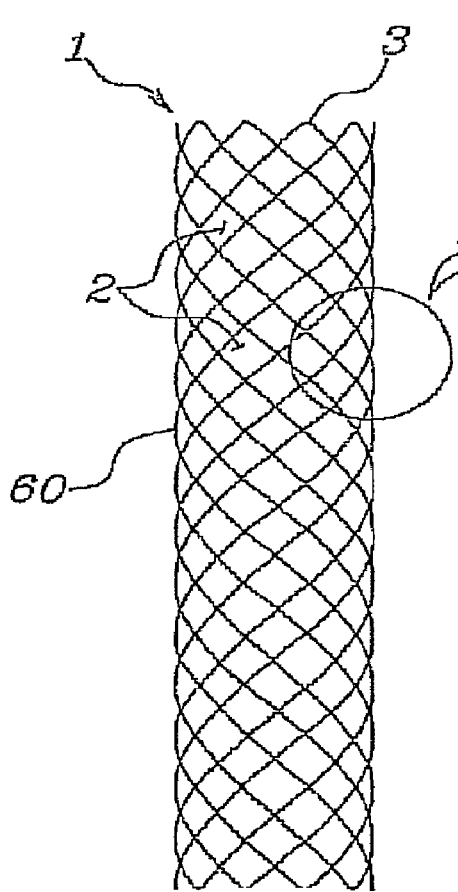
Figure 1B:
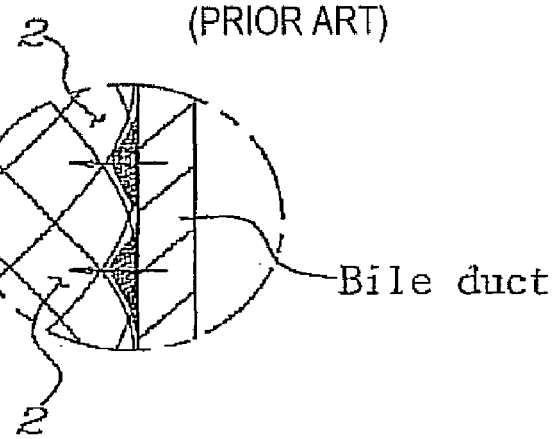

Reference will now be made in greater detail to a preferred embodiment of the invention, an example of which is illustrated in the accompanying drawings. Wherever possible, the same reference numerals will be used throughout the drawings and the description to refer to the same or like parts.

An embodiment of the present invention is characterized by a stent having a hollow cylindrical body that has a plurality of rhombic spaces formed by weaving a superelastic shape-memory-alloy wire so as to be crossed.

Figure 3:
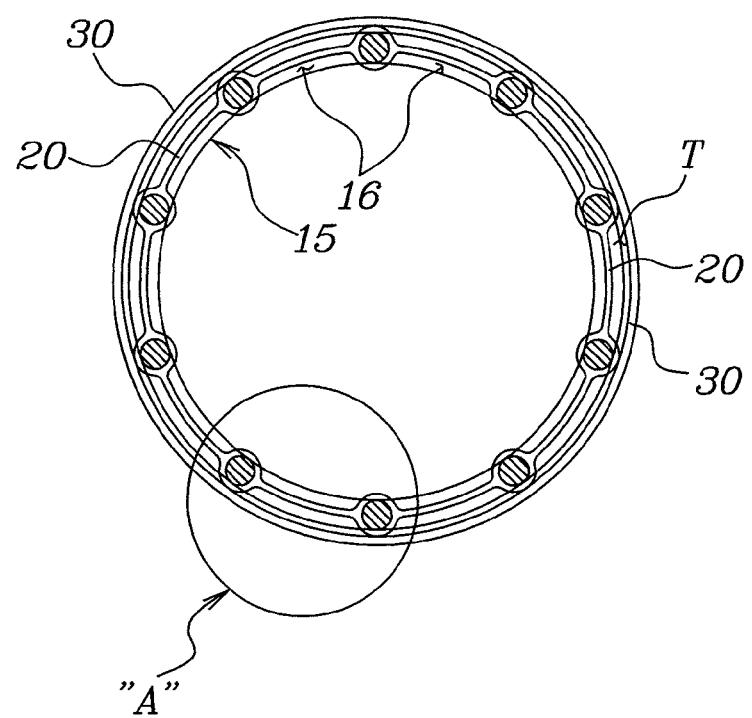
FIG. 3 is a side view of FIG. 2A.
Figure 4:
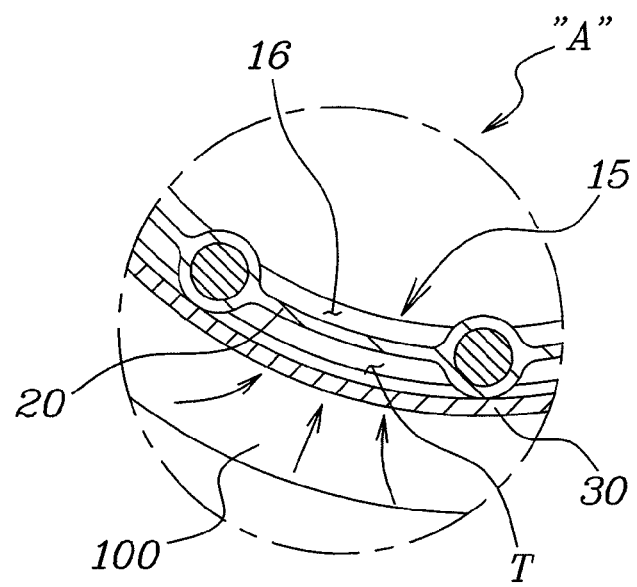
FIG. 4 is an enlarged view illustrating part A of FIG. 3.

As illustrated in FIGS. 2, 3 and 4, according to an embodiment of the present invention, a double-tube type stent has a hollow cylindrical body 15, which has a plurality of rhombic spaces 16 formed by weaving a superelastic shape memory alloy wire 60 so as to be crossed and which is coated with a thin film on an outer surface thereof.

At this time, the thin film includes a silicon coating layer 20 formed by immersing the cylindrical body 15 into a silicon solution or by spraying the silicon solution onto the cylindrical body 15.

A polytetrafluoroethylene (PTFE) tube 30 is fixedly fitted around the cylindrical body 15 having the silicon coating layer 20 leaving a gap T therebetween.

At this time, the PTFE tube 30 is tied to upper and lower ends of the cylindrical body 15 having the silicon coating layer 20 with a thread 40 such as a suture, and thereby is fixed to the cylindrical body 15.

Among the reference numerals which have not been yet described, 100 indicates a bile duct.

The operation and effects of the double-tube type stent configured as described above will be described below.

According to an embodiment of the present invention, the double-tube type stent is used to expand a hollow tubular organ such as a bile duct, an airway, an urethra, or an gullet when the hollow tubular organ, particularly, the bile duct on an anastomotic area of the intrahepatic bile duct of a liver transplant patient, is narrowed creating the chance of blocking a flow of bile. Particularly, the double-tube type stent forms the silicon coating layer and the PTFE tube on the outer surface thereof in a dual protection structure, thereby providing maximum durability and long-term usability in the bile duct, and preventing protrusion of a lesion area of the bile duct to block bleeding and enabling safe removal from the bile duct.

More specifically, the double-tube type stent includes the hollow cylindrical body 15, which has the plurality of rhombic spaces 16 formed by weaving the superelastic shape memory alloy wire 60 so as to be crossed, and which has the dual protection structure of the silicon coating layer and the PTFE tube on an outer surface thereof.

The silicon coating layer 20 is formed on the outer surface of the cylindrical body 15 by immersing the cylindrical body 15 into the silicon solution or by spraying the silicon solution onto the cylindrical body 15.

The PTFE tube 30 is fitted around the cylindrical body 15 having the silicon coating layer 20, and then is tied to the upper and lower ends of the cylindrical body 15 using the thread 40. Thereby, the PTFE tube 30 is fixed to the cylindrical body 15.

At this time, the gap T is formed between an inner surface of the PTFE tube 30 and the outer surface of the cylindrical body 15 due to a thickness of the wire 60 used for the stent.

As illustrated in FIG. 4, according to an embodiment of the present invention, the double-tube type stent is inserted at a position where the narrow tubular organ, particularly, the bile duct 100 is narrowed, causing the chance of blocking a flow of bile by a separate inserting device, thereby pushing the bile duct in an outward direction so as to expand the bile duct.

Above all, in the biliary stent according to an embodiment of the present invention, the PTFE tube 30 fitted around the cylindrical body 15 is not tied with the thread to the wire 60 forming the cylindrical body, but is tied with the thread 40 to the silicon coating layer 20. Thus, the thread is prevented from sliding, and thus maintains a firmly tied state.

Further, the strongly acidic bile in the bile duct 100 minimizes direct contact with the silicon coating layer 20, so that it is possible to prevent the silicon coating layer from being dissolved and damaged, which results in increasing durability.

Moreover, the silicon coating layer 20 and the PTFE tube 30 are formed in a dual protection structure, so that the PTFE tube 30 blocks the lesion area of the bile duct 100 from protruding inwards toward the cylindrical body 15 of the stent. Further, the gap T formed between the PTFE tube 30 and the silicon coating layer 20 serves as a resistor and a buffer, thereby effectively blocking the lesion area of the bile duct 100 from protruding inwards toward the cylindrical body 15 of the stent.

In other words, the double-tube type stent avoids a conventional problem whereby, since the lesion area of the bile duct 100 protrudes inwards toward the cylindrical body of the stent, the protruding parts must be cut off. Further, the double-tube type stent is easily removed from the bile duct without cutting off the protruding lesion area.

Thus, after the double-tube type stent has been inserted into the bile duct 100 for a long time, it can be easily removed from the bile duct unlike the prior art.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A double-tube type stent comprising:
    a hollow cylindrical body having a plurality of rhombic spaces formed by weaving a superelastic shape-memory-alloy wire so as to be crossed;
    a silicon coating layer coated on the outer surface of the cylindrical body using a silicon solution; and
    a polytetrafluoroethylene tube fixedly fitted around the cylindrical body, having the silicon coating layer, to form a plurality of gaps, wherein each gap is an empty space enclosed by portions of the silicon coating layer that are formed on the wire, portions of the silicon coating layer that cover the rhombic spaces between the wire, and the polytetrafluoroethylene tube, and wherein the plurality of gaps serve as buffers to inhibit a lesion from a duct into which the stent is inserted from protruding into the rhombic spaces of the hollow cylindrical body.

2. The double-tube type stent as set forth in claim 1 wherein the polytetrafluoroethylene tube is tied to upper and lower ends of the cylindrical body having the silicon layer with a thread so as to be fixed to the cylindrical body.

3. The double-tube stent as set forth in claim 2 wherein the polytetrafluoroethylene tube contacts the silicon layer only intermittently.

* * * * *